United States Patent [19]

Sayles

[11] Patent Number: 4,508,929
[45] Date of Patent: Apr. 2, 1985

[54] RECOVERY OF ALCOHOL FROM A FERMENTATION SOURCE BY SEPARATION RATHER THAN DISTILLATION

[75] Inventor: David C. Sayles, Huntsville, Ala.

[73] Assignee: The United States of America as represented by the Secretary of the Army, Washington, D.C.

[21] Appl. No.: 455,362

[22] Filed: Jan. 3, 1983

[51] Int. Cl.³ .................. C07C 29/76; C07C 29/86; C07C 31/08; C12P 7/06
[52] U.S. Cl. .................. 568/923; 435/161; 568/918; 568/920
[58] Field of Search .............. 435/161, 162, 163, 164, 435/165, 261; 568/918, 920, 923; 260/705

[56] References Cited

U.S. PATENT DOCUMENTS

| | | | |
|---|---|---|---|
| 2,053,770 | 9/1936 | Dreyfus | 435/161 |
| 2,492,098 | 12/1949 | Kelly | 568/918 |
| 4,262,149 | 4/1981 | Dotson, Jr. et al. | 568/923 X |
| 4,399,000 | 8/1983 | Tedder | 435/161 |

FOREIGN PATENT DOCUMENTS

| | | | |
|---|---|---|---|
| 0310623 | 5/1929 | United Kingdom | 568/918 |
| 0424135 | 2/1935 | United Kingdom | 435/161 |
| 2013716 | 8/1979 | United Kingdom | 435/162 |

OTHER PUBLICATIONS

*The Condensed Chemical Dictionary*, 10th Ed., New York, Van Nostrand Reinhold Co., 1981.
*Chemical Abstracts*, vol. 60, Abstract No. 1165c, Sergeeva et al., "The Salting Out Action of Calcium Chloride".
*Chemical Abstracts*, vol. 68, Abstract No. 48575d, Turevskaya et al., "Reaction of Magnesium Iodide with Alcohols in Ether Solutions".
Roddy, "Distribution of Ethanol-Water Mixtures to Organic Liquids", *Ind. Eng. Chem. Process Des. Dev.*, vol. 20, (1981), pp. 104–108.
Turevskaya et al., "Interaction of Magnesium Iodide with Alcohols in Ethereal Solutions", *Russian Journal of Inorganic Chemistry*, 17(12), 1972, pp. 1761–1762.

*Primary Examiner*—Esther M. Kepplinger
*Assistant Examiner*—Randall E. Deck
*Attorney, Agent, or Firm*—John H. Raubitschek; Werten F. W. Bellamy; Jack W. Voigt

[57] ABSTRACT

Ethanol is recovered from fermentation products by a countercurrent extraction process which employs diethyl ether as the extraction solvent to form a diethyl ether-ethanol mixture. The ethanol is salted out by adding calcium chloride to the mixture, and the diethyl ether layer is separated and recycled. The calcium chloride in ethanol solution is removed by adding sodium carbonate to form the solids calcium carbonate and sodium chloride which are removed by filtration. The ethanol is recovered as the filtrate.

1 Claim, 4 Drawing Figures

RECOVERY OF ALCOHOL FROM A FERMENTATION SOURCE BY SEPARATION RATHER THAN DISTILLATION

DEDICATORY CLAUSE

The invention described herein may be manufactured, used, and licensed by or for the Government for governmental purposes without the payment to me of any royalties thereon.

BACKGROUND OF THE INVENTION

The emphasis to develop alternate energy sources has particularly placed substitutes or extenders to gasoline on the high priority list. Of special interest is the use of ethanol in gasoline.

The cost of ethanol has been higher than the price of the gasoline to which it is added. This results in an additional increase in the price of the ethanol-gasoline blend. One such blend is commonly referred to as Gasohol. The sources from which ethanol can be derived by way of fermentation include grains, biomass, etc. A major portion of the cost of ethanol is related to distillation as a means of stripping the alcohol from the fermentation products. Distillation has one very serious limitation, and that is the large quantity of energy which must be consumed to effect the distillation. This large quantity of energy translates to higher costs for the distilled ethanol.

Advantages directly derived by a method for separation of ethanol by a non-distillation method would be the additional savings in energy and lower production costs in making ethanol more readily available as a diluent for gasoline. Both of the advantages would enhance the acceptance of a non-distillation method to replace currently employed methods of separation of ethanol by distillation. The cost advantage for separation should translate to a price advantage at the pump for Gasohol or ethanol-alcohol blend which has been proven by performance but not in its acceptance by the consumer because of the higher price for an alcohol-gasoline blend over an all gasoline fuel at today's prevailing prices.

An object of this invention is to provide a method for separation of ethanol from the fermentation products derived from the various possible sources, such as, grains, biomass, etc.

Another object of this invention is to provide a method for separation of ethanol from its fermentation products wherein countercurrent extraction procedures are employed and the materials employed to separate the ethanol are removed and recycled.

SUMMARY OF THE INVENTION

The method for separation of ethanol from the fermentation products derived from various sources, such as, grains, biomass, etc., in accordance with this invention, comprises a countercurrent extraction, involving the use of a solvent, such as, diethyl ether as the extractant for the ethanol. The ethanol is separated from the ether by a "salting out" process. The "salting out" is accomplished by adding anhydrous calcium chloride to the alcohol-ether mixture. The ether separates and is removed and recycled. The calcium chloride which remains dissolved in the ethanol is removed by the addition of sodium carbonate. The calcium chloride is then converted into calcium carbonate and sodium chloride. Both of these latter chemicals are insoluble in ethanol, and are removed by filtration.

DESCRIPTION OF THE PREFERRED EMBODIMENT

A fermentation products source of the type employed for distillation technique for removal of ethanol, except that in accordance with the preferred embodiment of this invention a countercurrent extraction method is employed to extract the ethanol from the fermentation products which can be derived from various sources, such as, grains, biomass, etc. The method involves the use of a solvent, diethyl ether as the extractant for the ethanol.

Figure 3:
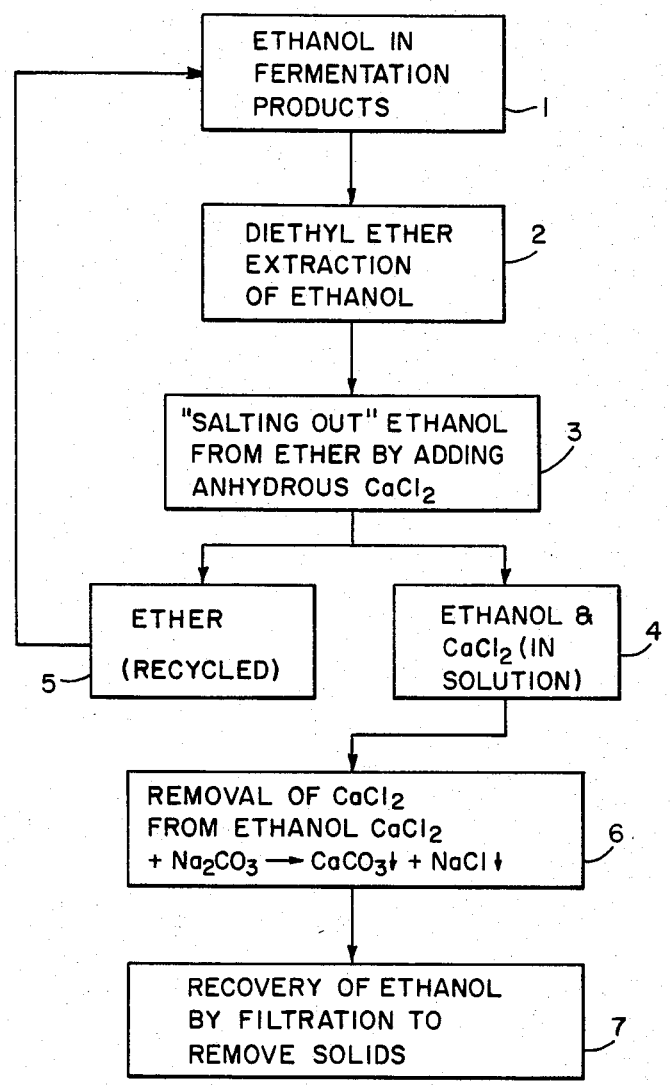
FIG. 3 of the drawing depicts a countercurrent extraction method of ethanol by diethyl ether from fermentation products, the subsequent recycling of ether after "salting out" of ethanol by $CaCl_2$, the removal of $CaCl_2$ by adding $Na_2CO_3$, and the removal of ethanol by filtration to remove the solids $CaCO_3$ and NaCl.

FIG. 3 of the drawing depicts ethanol in fermentation products (1), extraction step by diethyl ether (2), the salting out step employing $CaCl_2$ to remove the ethanol from the diethyl ether (3), ethanol and $CaCl_2$ in solution (4), the recycling of the diethyl ether (5), the removal of $CaCl_2$ from the ethanol by adding $Na_2CO_3$ to form the solids $CaCO_3$ and NaCl (6), and a filtration step to remove the solid and recover the ethanol as the filtrate (7).

The "salting out" step is accomplished by adding anhydrous calcium chloride to the alcohol-ether mixture. The ether separates and is removed and recycled. The calcium chloride is removed from the ethanol by filtration after sodium carbonate is added to form calcium carbonate and sodium chloride in accordance with the following reaction:

$$CaCl_2 + Na_2CO_3 \rightarrow CaCO_3 + 2NaCl.$$

The ethanol is recovered as the filtrate.

EXAMPLE I

In order to demonstrate this process for the recovery of alcohol, a dilute aqueous solution which simulated the industrial alcohol "beer" as it would come out of the fermenter used in the conversion of molasses into industrial alcohol was prepared. The simulated beer consisted of ethanol (95%, 100 ml), diluted with 500 ml water. This mixture was placed in a separatory funnel. Diethyl ether (100 ml) was added, and the resulting ether-alcohol solution was separated. Anhydrous calcium chloride was added to the mixture, and the ethanol-calcium chloride solution was separated. Sodium carbonate was then added to the solution, and the precipitate, consisting of calcium carbonate and sodium chloride was separated by filtration. The supernatant liquid was filtered. The yield of recovered alcohol proved to be 98–99%.

Figure 1:
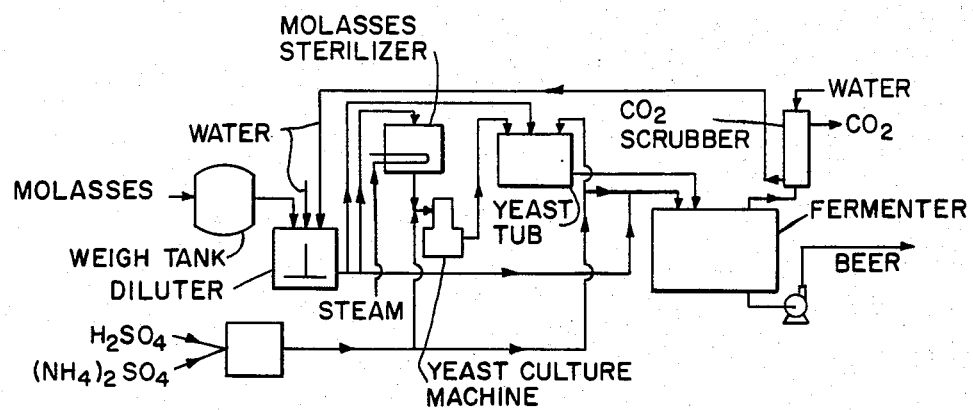
FIG. 1 of the drawing depicts a flow chart for the manufacture of Industrial Alcohol "beer" or a fermentation source containing ethanol.

The process for the preparation of industrial alcohol "beer" from molasses or other fermentable raw materials can be accomplished using the following procedure and with additional reference to the drawing, FIG. 1, wherein:

(1) Molasses, from the weigh tank, is transferred to a diluter where it is diluted with water;

(2) The molasses solution is then transferred to the steam-heated molasses sterilizer;

(3) Yeast which has been transferred from the yeast culture machine is transferred to the yeast tub where the pH is adjusted by the addition of aqueous solutions of ammonium sulfate and sulfuric acid;

(4) The mixture is then transferred to the fermenter;

(5) The output from the fermenter is the industrial alcohol "beer".

EXAMPLE II

In order to compare the process of this invention with the prior art distillation process, the total ethanol in the fermentation products was determined by removing a representative sample of the industrial alcohol "beer" and removing the ethanol from it by steam distillation. The steam distillate is then stripped of ethanol by fractional distillation through an efficient Vigreaux column (10-inches in length). The 95% aqueous alcohol yield was compared with that obtained by extraction, salting out with calcium chloride, and precipitation of the calcium chloride from the ethanol by sodium carbonate. The yield of ethanol from the distillation process was of the order of 94–96% whereas the extraction process was 98–99%.

TABLE I

MATERIALS, ENERGY, LABOR REQUIREMENTS PER GALLON OF 95% (190 PROOF) INDUSTRIAL ALCOHOL

|  | DISTILLATION PROCESS | EXTRACTION PROCESS |
|---|---|---|
| Molasses (gal) | 2.5 | 2.5 |
| Sulfuric Acid (60° Be) (lb) | 0.17 | 0.17 |
| Ammonium Sulfate (lb) | 0.015 | 0.015 |
| Steam (lb) | 40. | 5. |
| Process Water (gal) | 10. | 18. |
| Cooling Water (gal) | 42. | 0. |
| Electricity (Kw-hr) | 0.11 | 0.01 |
| Direct Labor (labor-hr) | 0.05 | 0.02 |

Example I illustrates the high yield of recovered alcohol and Table I illustrates the savings of materials, energy, and labor per gallon of 95% (190 Proof) industrial alcohol recovered by extraction process.

Figure 2:
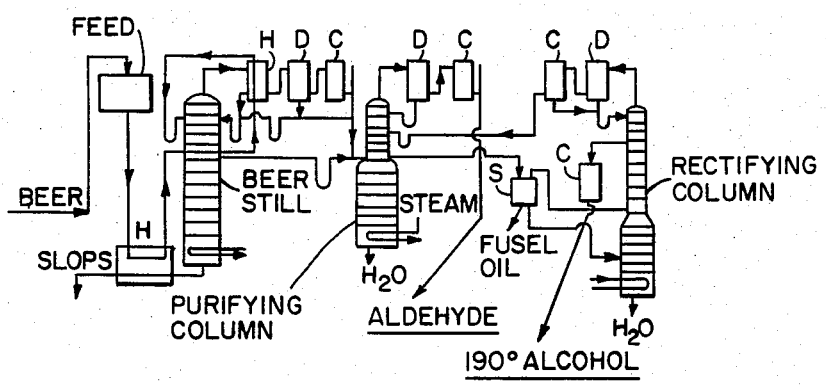
FIG. 2 of the drawing depicts a flow chart for recovery of alcohol by distillation.

In further reference to the drawing, FIG. 2, the code letters are defined as follows:

C = Condenser
D = Dephlegmator
H = Heat Exchanger
S = Separator

Figure 4:
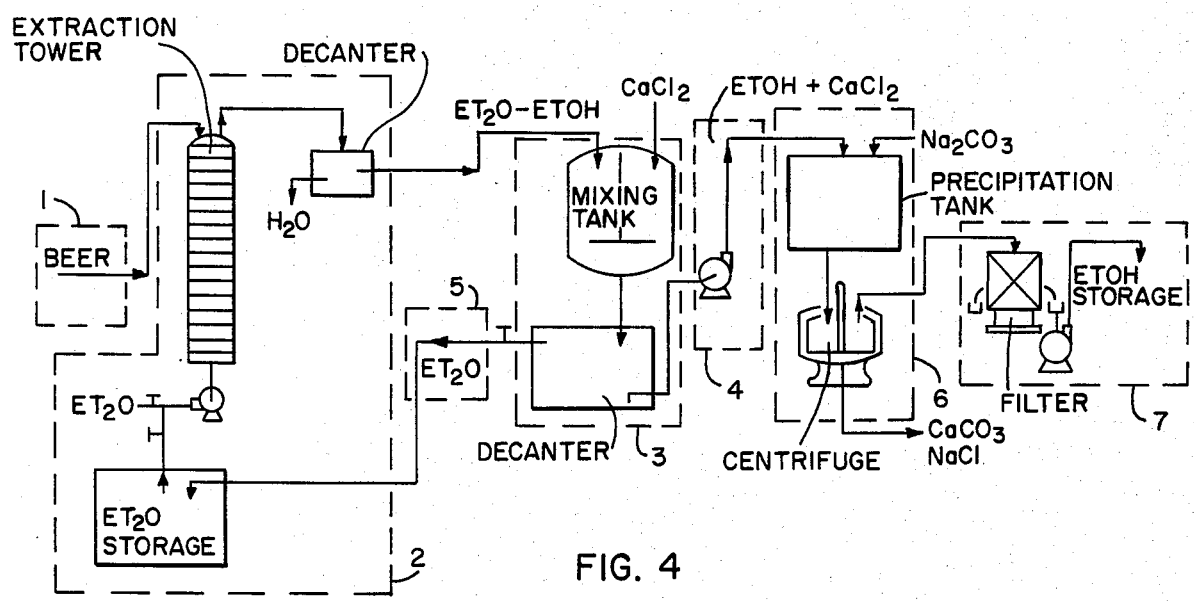
FIG. 4 of the drawing depicts a schematic drawing to illustrate the extraction method of FIG. 3 in accordance with equipment employed in carrying out the extraction of ethanol from a fermentation source.

In further reference to the drawing, FIG. 4, the flow chart steps depicted in FIG. 3 are depicted in FIG. 4 by like numerals to relate the steps of the extraction method to the equipment illustrated to carry out the steps shown.

I claim:

1. A method of recovering ethanol from a fermentation source by separation rather than by distillation, said method comprising:

i. providing a fermentation source which contains ethanol in a mixture of fermentation products in said fermentation source;

ii. extracting said ethanol by countercurrent extraction with diethyl ether to yield an ethanol-diethyl ether mixture;

iii. employing a salting out process which comprises adding anhydrous calcium chloride to said ethanol-diethyl ether mixture to form a diethyl ether layer and an ethanol-calcium chloride solution layer;

iv. removing said $CaCl_2$ from said ethanol-calcium chloride solution by adding sodium carbonate to yield the solids calcium carbonate and sodium chloride; and v. filtering said ethanol to remove solids of calcium carbonate and sodium chloride and recovering said ethanol as the filtrate.

* * * * *